United States Patent
Chavan et al.

(10) Patent No.: US 11,432,812 B2
(45) Date of Patent: Sep. 6, 2022

(54) KNOTLESS ANCHOR ASSEMBLY AND METHODS THEREOF

(71) Applicant: Dunamis, LLC, Greenville, AL (US)

(72) Inventors: Prithviraj Chavan, Greenville, AL (US); Eugene Shoshtaev, Greenville, AL (US)

(73) Assignee: Dunamis Medical Technologies, LLC, Greenville, AL (US)

( * ) Notice: Subject to any disclaimer, the term of this patent is extended or adjusted under 35 U.S.C. 154(b) by 259 days.

(21) Appl. No.: 16/410,794

(22) Filed: May 13, 2019

(65) Prior Publication Data

US 2019/0343507 A1 Nov. 14, 2019

Related U.S. Application Data

(60) Provisional application No. 62/670,438, filed on May 11, 2018.

(51) Int. Cl.
*A61B 17/04* (2006.01)

(52) U.S. Cl.
CPC .... *A61B 17/0401* (2013.01); *A61B 2017/044* (2013.01); *A61B 2017/0433* (2013.01)

(58) Field of Classification Search
CPC ............ A61B 17/0401; A61B 17/8685; A61B 2017/0433; A61B 2017/044; A61F 2002/0823; A61F 2/0811
USPC ......................................................... 606/232
See application file for complete search history.

(56) References Cited

U.S. PATENT DOCUMENTS

| 6,840,953 B2 * | 1/2005 | Martinek ........... A61B 17/0401 606/232 |
| 2006/0241594 A1 | 12/2006 | McCarthy et al. |
| 2007/0233075 A1 | 10/2007 | Dawson |
| 2009/0326579 A1 | 12/2009 | Anderhub et al. |
| 2013/0006302 A1 * | 1/2013 | Paulk ................ A61B 17/0401 606/232 |
| 2014/0257381 A1 * | 9/2014 | Palese ............... A61B 17/0401 606/232 |

(Continued)

FOREIGN PATENT DOCUMENTS

| WO | 2010132309 | 11/2010 |
| WO | 2013151817 | 10/2013 |

OTHER PUBLICATIONS

PCT/US2019/032037 International Search Report dated Jul. 22, 2019.

(Continued)

*Primary Examiner* — Kathleen S Holwerda
*Assistant Examiner* — Lauren Dubose
(74) *Attorney, Agent, or Firm* — Jay B. Bell (57) ABSTRACT

A knotless anchor assembly method and device comprising an anchor and a compression member, wherein the anchor further comprises a pilot tip and anchor body. During procedures to tension the knotless anchor assembly, the anchor is driven into bone or other surface or component, and the tension member is urged into the anchor body recess. The compression member is secured in the anchor body to lock the tension member in place. The knotless anchor assembly gives the surgeon or user the ability to optimize tensioning by having the ability to change tension in the tension member by adjusting the compression member during or after the repair.

16 Claims, 11 Drawing Sheets

(56) References Cited

U.S. PATENT DOCUMENTS

| | | | |
|---|---|---|---|
| 2016/0022341 A1* | 1/2016 | Agarwal | A61B 17/7037 606/308 |
| 2016/0310127 A1* | 10/2016 | Cavallazzi | A61B 17/0401 |
| 2018/0008256 A1 | 1/2018 | Fallin | |

OTHER PUBLICATIONS

E. Pennisi, Tending tender tendons, Science 80 (295) (2002) 1011.

Maffulli N, Wong j, Almekinders LC. Types and epidemiology of tendinopathy. Clin Sports Med 2003;22 (4): 675-92.

Cho NS, Lee BG, Rhee YG, Arthroscopic rotator cuff repair using a suture bridge technique: Is the repair integrity actually maintained? Am J Sports Med 2011;39:2018-2116.

Christoforetti JJ, Krupp RJ, Singleton SB, Kissenberth MJ, Cook C, Hawkins RJ. Arthroscopic suture bridge transosseous equivalent fixation of rotator cuff tendon preserves intratendinous blood flow at the time of initial fixation. J Shoulder Elbow Surg 2012;21:523-530.

Kim SH, Kim J, Choi Ye, Lee HR, Healing disturbance with suture bridge configuration repair in rabbit rotator cuff tear. J Shoulder Elbow Surg 2016;25:478-486.

Kullar RS, Reagan JM, Kolz CW, Burks RT, Henninger HB. Suture placement near the musculotendinous junction in the supraspinatus: Implications for rotator cuff repair. Am J Sports Med 2015;43:57-62.

Virk MS, Bruce B, Hussey KE, et al. Biomechanical performance of medial row suture placement relative to musculotendinous junction in transosseous equivalent suture bridge double-row rotator cuff repair. Arthroscopy 2017;33:242-250.

Peter J. Millet, Zaamin B Hussain, Erik M Fritz, Ryan J Warth, J. Cristoph Katthagen, Jonas Pogorzelski Rotator Cuff Tears at the Musculotendinous Junction: Classification and Surgical Options for Repair and Reconstruction.

Kurtz SM, Devine JN. PEEK Biomaterials in Trauma, Orthopedic, and Spinal Implants. Biomateials. 2007;28(32):4845-4869. doi:10.1016/j.biomaterials.2007.07.013.

F. Alan Barber, David B. Spenciner, Samir Bhattacharyya, Larry E. Miller Arthroscopy Biocomposite Implants Composed of Poly(Lactide-co-Glycolide)/ β-Tricalcium Phosphate: Systematic Review of Imaging, Complication and Performance Outcome.

Baker, B. (2015). MedTech360: Sports Medicine Devices, US, 2016, Market Analysis. Millennium Research Group, Inc.

Burkhart SS1, Johnson TC, Wirth MA, Athanasiou KA Arthroscopy. Apr. 1997;13(2):172-6 Cyclic loading of transosseous rotator cuff repairs: tension overload as a possible cause of failure.

Mazzocca AD, Millett PJ, Guanche CA, Santangelo SA, Arciero RA. Arthroscopic single-row versus double-row suture anchor rotator cuff repair. Am J Sports Med 2005;33:1861-1868.

Denard PJ, Jiwani AZ, Lädermann A, Burkhart SS. Long-term outcome of arthroscopic massive rotator cuff repair: The importance of double-row fixation. Arthroscopy 2012;28:909-915.

Park JY, Lee SY, Chung SW, Zulkifi H, Cho JH, Oh KS. Clinical comparison between double-row and transosseous-equivalent repairs for medium to large size rotator cuff tears. Arch Orthop Trauma Surg 2013;133:1727-1734.

Vaishnav S, Millett PJ. Arthroscopic rotator cuff repair: Scientific rationale, surgical technique, and early clinical and functional results of a knotless self-reinforcing double-row rotator cuff repair system. J Shoulder Elbow Surg 2010;19:83-90.

Park MC, Biomechanical validation of rotator cuff repair techniques and considerations for "technical efficiency ratio". Arthroscopy 2013;29:1230-1234.

Park MC, Peterson A, Patton J, McGarry MH, Park CJ, Lee TQ. Biomechanical effects of a 2 suture-pass medial intermplant mattress on transosseous-equivalent rotator cuff repair and considerations for a "technical efficiency ratio". J Shoulder Elbow Surg 2014;23:361-368.

Yamakado K, Katsuo S, Mizuno K, Arakawa H, Hayashi S. Medial-row failure after arthroscopic double-row rotator cuff repair. Arthroscopy 2010;26:430-435.

Cho NS, Yi JW, Lee BG, Rhee YG. Retear patterns after arthroscopic rotator cuff repair: single-row versus suture bridge technique. Am J Sports Med. 2010;38(4):664-71.

Bukhart SS, Adams CR, Bukhart SS, Schoolfield JD. A biomechanical comparison of footprint reconstruction for rotator cuff repair: The SwiveLock-FibreChain construction versus standard double-row repair. Arthroscopy 2009;25:274-281.

Voluntary Amendments filed in European Counterpart, EP19800267.7 (NS-PCT of PCT/US2019/032037), Filed Jun. 28, 2021.

Supplemental European Search Report, EP19800267.7 (NS-PCT of PCT/US2019/032037), dated Jan. 25, 2022.

* cited by examiner

KNOTLESS ANCHOR ASSEMBLY AND METHODS THEREOF

CROSS-REFERENCE TO RELATED APPLICATIONS

This application claims priority to U.S. Provisional Application No. 62/670,438 filed on May 11, 2018, the contents of which are incorporated herein by reference in its entirety.

FIELD OF THE INVENTION

The present invention is related to tissue repair. Specifically, the invention is related to an improved knotless anchor assembly and method of securing tissue, ligaments, sutures, grafts, allografts, membrane, gap fillers, tension members or bone to bone in stabilization procedures.

BACKGROUND

Tendon, ligament and joint capsular injuries account for 45% of the orthopedic injuries which seek medical attention (Pennisi, 2002). Tendon injuries alone effect 30 million people annually (Wong, 2003), resulting in an enormous amount of physical and financial burden to both the individuals and the economy. Most of the affected people are treated with surgical repair or reconstruction to avoid long-term disability and pain relief. Tears can be primary and related to an injury or secondary and related to a re-tear after a primary repair or surgery. There has been an increased incidence of secondary tears and a large proportion of them may be avoided by using a better device to perform the procedure.

Secondary or type 2 failure occurs where the tendon fails medially to the repair, close to the muscle tendon attachment (Cho et al., 2011; Christoforetti et al., 2012; Kim et al., 2016; Kullar et al., 2015; Virk et al., 2017; Cho et al., 2010). Secondary medial cuff failure near the muscle tendon attachment after repair (type 2 failure) has been associated with the placement of knots and abrasive suture materials near the muscle tendon attachment, thus, potentially resulting in acute or chronic subacromial knot impingement, medial row stress concentration, tendon strangulation, and/or suture cut-out in this area (Cho et al., 2011; Christoforetti et al., 2012; Kim et al., 2016; Kullar et al., 2015; Virk et al., 2017). When failure occurs, the tendon/muscle is found to be torn medial to the previous repair site of the cuff tendon insertion (Cho et al., 2011; Christoforetti et al., 2012; Kim et al., 2016; Kullar et al., 2015; Virk et al., 2017).

Studies suggest that primary prevention can address secondary type 2 re-tears, and techniques such as utilizing knotless, linked and bridging constructs have been developed to prevent tissue strangulation and improve force distribution (Mazzocca et al., 2005; Denard et al., 2012). The use of tapes with these knotless repairs also decreases the compressive stress per unit area of tendon (Park et al., 2013; Vaishnav et al., 2010). The lack of knots avoids the possibility of acute or chronic postoperative knot impingement within the subacromial space (Yamakado et al., 2010), decreases operative time (Bukhart et al., 2009) and improves efficiency (Park, 2013; Park et al., 2014). Studies also suggest that rotator cuff tears that are repaired with a "tension overload mechanism" over a portion of the muscle-tendon units will undergo gradual failure with physiologic cyclic loading. Therefore, tendons should be repaired without tension if possible (Burkhart et al., 1997).

Several factors currently lead to an increased failure of repair. They are mainly a) knots causing impingement (Yamakado et al., 2010) and b) problems related to tensioning of repair, which can lead to strangulation of tissue causing necrosis over time, increased stresses on the anchoring device and failure with suture pulling out through tissue (Park, 2013; Park et al., 2014; Mazzocca et al., 2005; Denard et al., 2012).

Knotless anchors currently in the market only address knot related problems but continue to have other limitations whereby they either must be used in combination with another system, such as a secondary anchor, have limitation of the number of fibers passing through the anchor and continue to have major challenges related to tissue tensioning. These deficiencies hinder the surgeon's ability to adjust tissue tension at the time of repair or readjust once the repair is complete. This leads to under tensioning and failure due to gap formation or over-tensioning of the repair and failure at repair site, strangulation of blood supply to the tissue and re-tear. Thus, a need exists for a knotless anchor assembly that doesn't require a secondary anchor and allows for tension adjustment at the time of repair.

BRIEF DESCRIPTION OF THE DRAWINGS

Further advantages of the invention will become apparent by reference to the detailed description of preferred embodiments when considered in conjunction with the drawings:

FIGS. 1A-1B depict a perspective views of the first embodiment of the knotless anchor assembly. Individually.

FIGS. 2A-B depict embodiments of the pilot tip. Individually.

FIGS. 3A-3D depict views of the first embodiment of the knotless anchor assembly. Individually.

FIG. 4A-4C depict perspective views of the first embodiment of the knotless anchor assembly. Individually, FIG. 4A depicts a perspective view of the first embodiment of the knotless anchor assembly with broach/pusher. FIG. 4B depicts a perspective view of the first embodiment of the knotless anchor assembly. FIG. 4C depicts a perspective view of the first embodiment of the knotless anchor assembly.

FIG. 5A-5C depict views of an alternative method of the first embodiment of the knotless anchor assembly. Individually.

FIGS. 6A-6E depict views of the second embodiment of the knotless anchor assembly. Individually.

FIGS. 7A-7D depict views of the third embodiment of the knotless anchor assembly. Individually.

FIGS. 8A-8E depict views of the third embodiment of the knotless anchor assembly. Individually.

FIGS. 9A-9E depict views of the fourth embodiment of the knotless anchor assembly. Individually.

FIGS. 10A-10E depict views of the fifth embodiment of the knotless anchor assembly. Individually.

FIGS. 11A-11D depict views of the sixth embodiment of the knotless anchor assembly. Individually.

FIGS. 12A and 12B depict an embodiment of the anchor. Individually, FIG. 12B depicts an embodiment of an anchor.

SUMMARY OF THE INVENTION

Knotless assemblies that secure bone and tissue fragments can lose tension or over tension before the assemblies can lock or at the time of locking resulting in inefficient placement of the assembly during surgical procedures. The presently disclosed invention is a method and device comprising an anchor and a compression member, wherein the anchor further comprises a first end, second end and anchor body. During procedures to tension the knotless anchor assembly, the anchor is driven into bone, and the tension member is urged into the anchor body recess. The compression member is secured to the anchor body to lock the tension member in place. The knotless anchor assembly gives the surgeon or user the ability to optimize tensioning by having the ability to change tension in the tension member(s) by adjusting the compression member and does not require the use of an additional system, such as a secondary anchor.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

Knotless anchors in the prior art hinder surgeons' ability to adjust tissue tension at the time of repair or readjust once the repair is complete resulting in under tensioning and failure due to gap formation or over-tensioning of the repair and failure at repair site, strangulation of blood supply to the tissue and re-tear. The knotless anchor assembly disclosed herein 32 allows the surgeon to adjust the repair tension based on the tissue biology of the tendon and, hence, optimizes the mechanical construct of the repair by providing a stable tension free repair. This reduces failures of repair due to inappropriate soft tissue tensioning. Further, surgical cost will be reduced due to decreasing the number of devices needed for the procedure, as the knotless anchor assembly 32 can be used independently and does not require other systems or anchors. The knotless anchor assembly 32 allows more sutures to pass through the anchor body and reduces the operative time since it eliminates the need for knot tying.

Additionally, the knotless anchor assembly can be used as a self-tapping anchor and can have multiple threaded components to increase the pull-out force. Several embodiments allow the surgeon or user performing the procedure to modify the repair during or after implanting the anchor body in the bone by adding more tension members and changing the size of the compression member, if required. Actively controlling the process of the repair during the repair provides an ultimate repair construct.

Figure 1A:
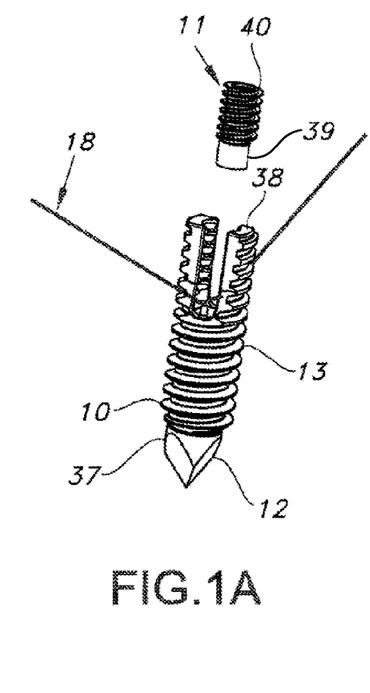
FIG. 1A depicts a perspective view of the compression member and anchor with tension member in the anchor body recess.
Figure 1B:
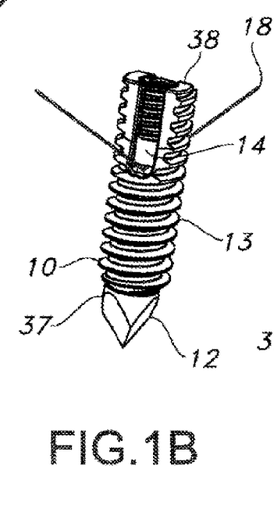
FIG. 1B depicts a perspective view of the compression member inside the anchor body recess.
Figure 1C:
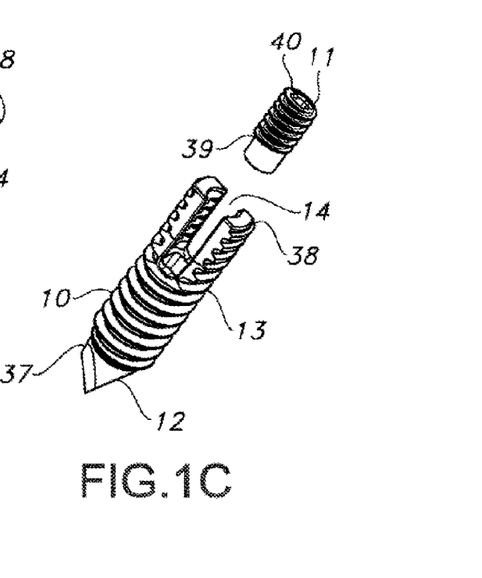
FIG. 1C depicts a perspective view of the compression member and anchor body.

The knotless anchor assembly disclosed herein 32 comprises an anchor 10 and a compression member 11, as shown in FIGS. 1A-1C, and secures tissue, ligaments, sutures, grafts, allografts, membrane, gap fillers, tension members or bone to bone in stabilization procedures. The anchor 10 further comprises a pilot tip 12 and anchor body 13, as shown in FIG. 1A.

To utilize the knotless anchor assembly 32, the anchor 10 is driven into bone 30 lead by the pilot tip 12, and the tension member 18 is urged into the anchor body recess 14. The compression member 11 is then threaded into the mating thread 17 of the anchor body 13 or otherwise secured in the anchor body 13 to lock the tension member 18 in place, as shown in FIGS. 1B and 5C. Backing out the compression member 11 completely or partially allows for unlocking of the tension member 18 and adjustment before re-locking. The anchor 10 can be used with a different assembly tool used to implant the anchor 10 or knotless anchor assembly 32. Other techniques besides a coupling instrument or tool may be used to drive the compression member 11 to cause locking of the knotless anchor assembly 32.

For the first embodiment of the knotless anchor assembly 32 depicted in FIG. 1, the compression member 11 may secure the tension member 18 or other fixation member that pass through the anchor body recess 14 by downward migration using multiple mechanisms, including, but not limited to, threading, to secure the tension members 18 using the compression member 11. The locking or securing of the compression member 18 may happen in multiple locations. For example, the knotless anchor assembly 32 may contain pinching points between the compression member 11 and the anchor body 13 or a combination of pinching points and compression by the first or distal end 39 of the compression member 11 or first or distal end 39 of the compression member 11 sitting on a base contained within the anchor body recess 14, or it can be a combination of fixation between pinching points and the second end 38 of the anchor body 13 or a base within the anchor body recess 14 or other fixation point that may be created by this downward migration of the compression member 18. The location of the fixation points or base within the anchor body recess 14 or location of security of the tension members may vary within the anchor 10 itself.

The anchor body 13 of the anchor 10 defines a longitudinal axis, and further comprises a first end 37 consisting of a bone engaging feature and a second end 38 consisting of a feature to couple to the compression member 11. The anchor body 13 may include an anchor body recess 14 traversing at least part of the anchor body 13 between the first end 37 and second end 38 of the anchor body. The second end 38 of the anchor body 13 may be partial or complete, may have a cannulation slot or openings necessary for the knotless anchor assembly 32 to perform its function. Also, the base within the anchor body recess 14 may be partial or complete or may have holes or slots.

The compression member 11 also defines a longitudinal axis and further comprises a first or distal end 39 consisting of comprising a feature to couple the compression member 11 to the anchor body 13, a second or proximal end 40 comprising a feature to couple to an instrument. The compression member 11 may be comprised of multiple individual components.

Figure 2A:
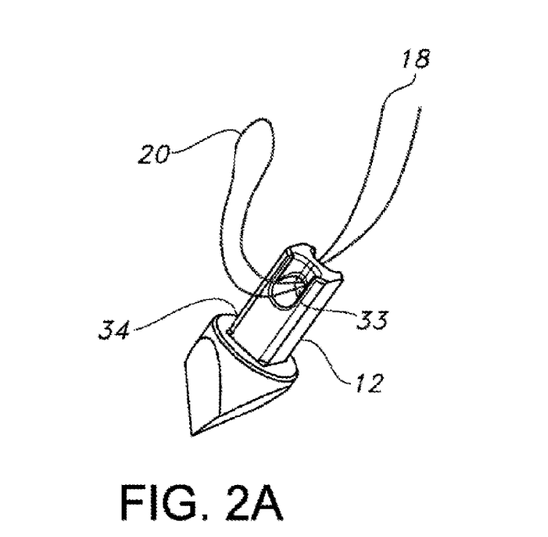
FIG. 2A depicts a perspective view of an embodiment of a pilot tip.
Figure 2B:
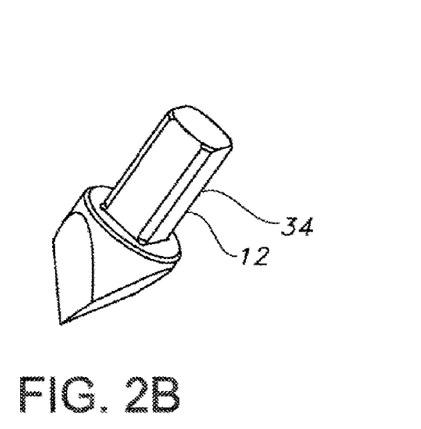
FIG. 2B depicts a perspective view of an embodiment of a pilot tip.
Figure 3A:
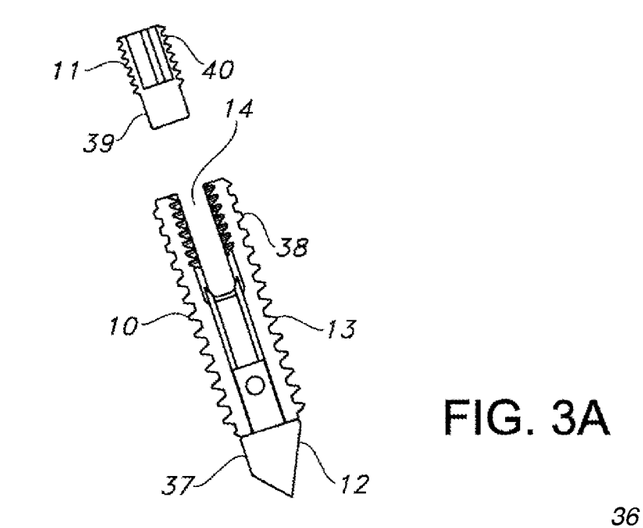
FIG. 3A depicts a cross-sectional view of the first embodiment of the knotless anchor assembly.
Figure 3B:
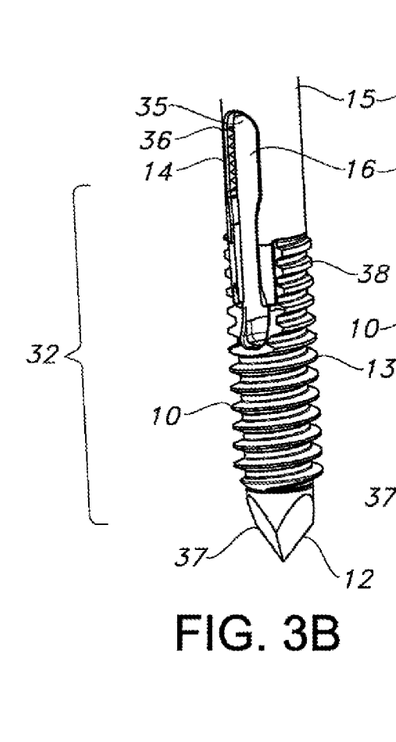
FIG. 3B depicts a perspective view of the first embodiment of the knotless anchor assembly with a sleeve.
Figures 3C, 3D:
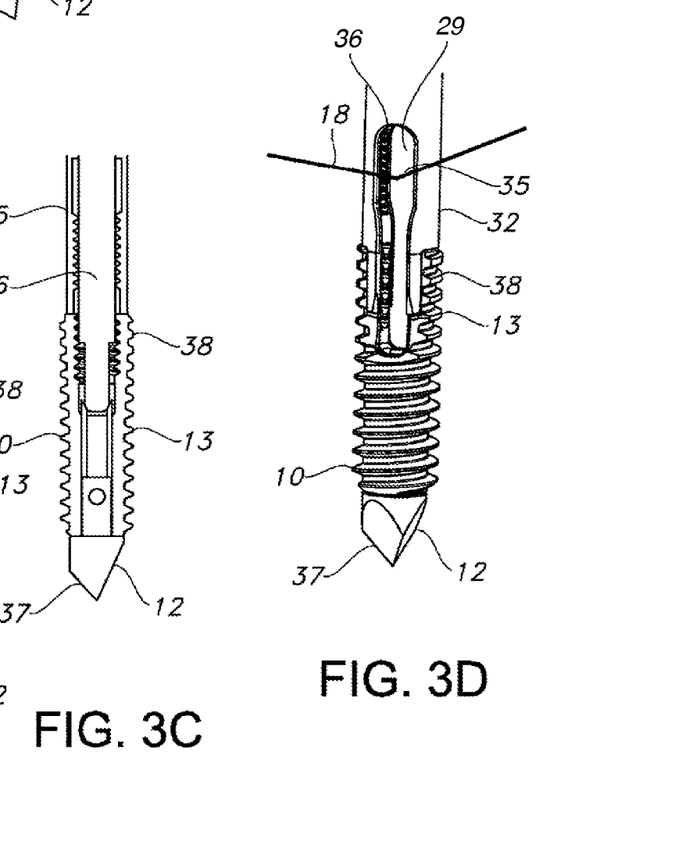
FIG. 3C depicts a cross-sectional view of the first embodiment of the knotless anchor assembly with sleeve.
FIG. 3D depicts a perspective view of the first embodiment of the knotless anchor assembly with sleeve.

The first end 37 of the anchor 10 may further comprise a pilot tip 12 that leads the anchor 10 into the bone 30, or the anchor 10 can be implanted using a tool or be self-punching or otherwise self-engaging. The pilot tip 12 may or may not assist with tensioning the knotless anchor assembly 32. The pilot tip 12 may or may not be made out of the same material as the anchor and can be made from other materials typically used in the industry. The pilot tip 12 and anchor 10 may be manufactured as one unit using standard manufacturing process used in the industry, or the pilot tip 12 can be manufactured separately from the anchor 10 and later on assembled on the anchor body 13. The pilot tip 12 may be different shapes depending on the force needed for insertion. The pilot tip 12 may vary in length depending on the location and anatomy of the application. The pilot tip 12 or part of the pilot tip 12 may be solid and non-cannulated, as shown in FIG. 2B, or be cannulated through the core, have slots or grooves, or have a partial or complete hole 33 through the body 34 of the pilot tip 12 or some location within the pilot tip 12, as shown in FIG. 2A. The pilot tip 12 may also be manufactured in a process which requires it to be connected to the anchor 10, e.g. press fit, mold, twist, threads, overlay on the anchor 10 or by other processes of manufacturing to achieve the same outcome and function.

Figures 4A, 4B, 4C:
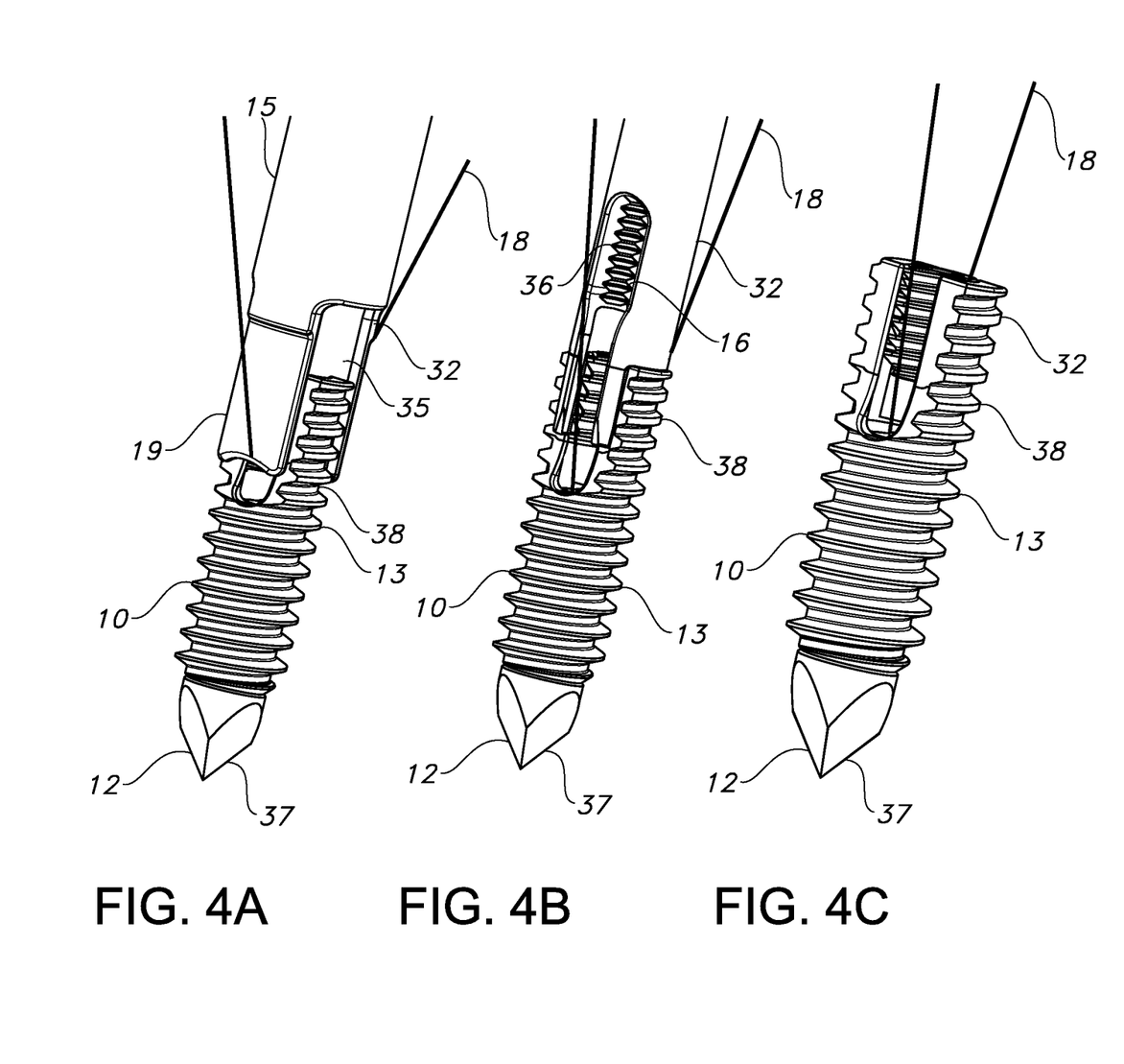
Figure 5A:
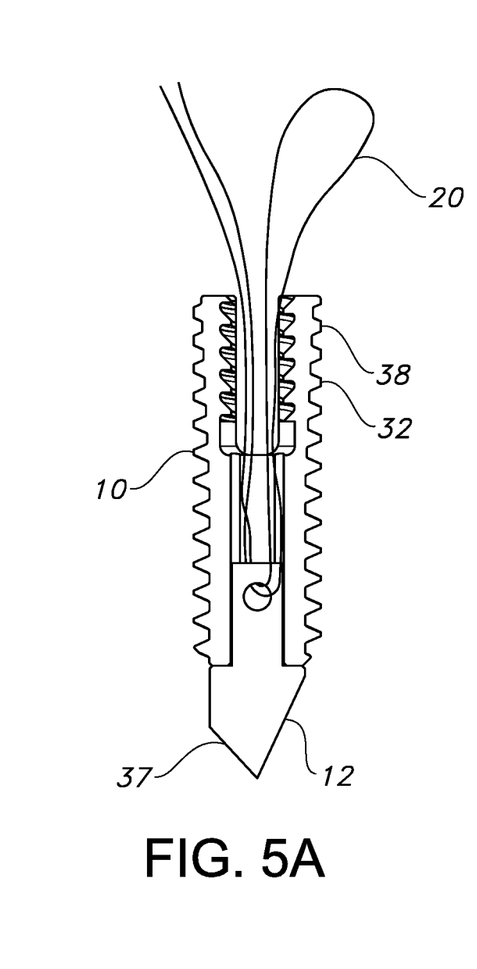
FIG. 5A depicts a cross-sectional view an alternative method of the first embodiment of the knotless anchor assembly with passing loop.
Figure 5B:
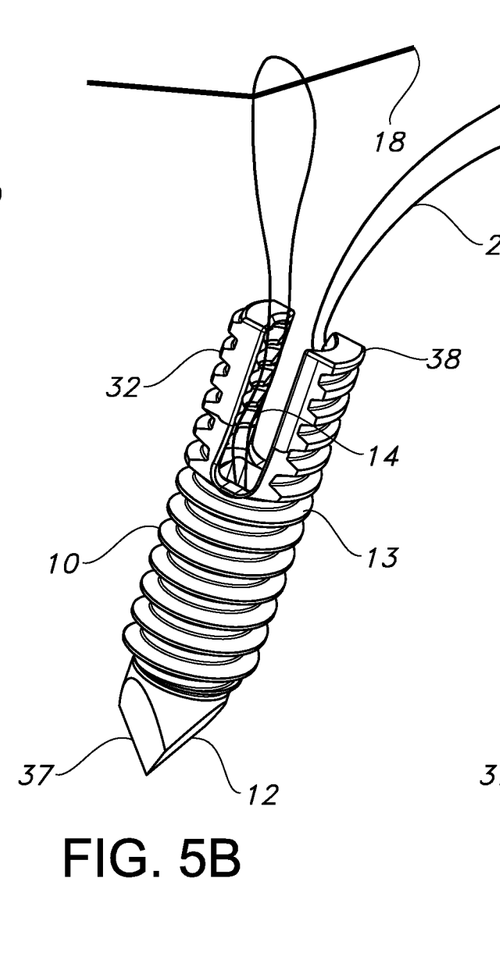
FIG. 5B depicts a perspective view of an alternative method of the first embodiment of the knotless anchor assembly.
Figure 5C:
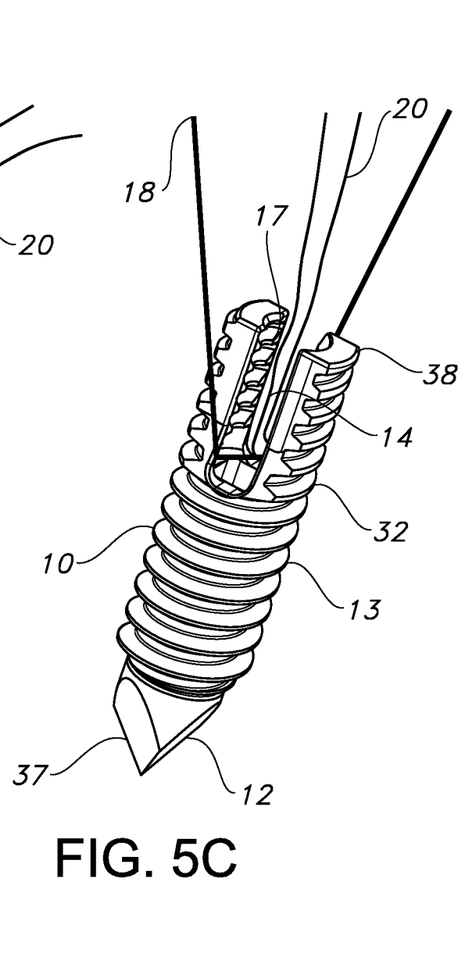
FIG. 5C, depicts a perspective view of an alternative method of the first embodiment of the knotless anchor assembly.

The tension member 18 may pass through the anchor body recess 14 directly or pass through the anchor body recess 14 and the hole 33 in the body 34 of the pilot tip 12, as shown in FIG. 2A and FIG. 5A. The tension member 18 can be part of suture material or fixation member of soft tissue shown in FIG. 5A or it can also be a passing loop, as shown in FIGS. 5A and 5B. The compression member 11 may be a part of the knotless anchor assembly 32 at the time of anchor 10 implantation, as shown FIG. 1B, or it can be part of the tool or sleeve 15 shown in FIGS. 3 and 4 or similar tool that be used as a single tool connected to the anchor 10 or multiple tools that can connect to the anchor body 10. After deployment, the compression member 11 may finally end up in the anchor body 10 to form a knotless anchor assembly 32.

It is contemplated herein that the compression member 11 may be inserted later or replaced with one of a different size, using a separate tool for its insertion. In this embodiment, the compression member 11 is not part of anchor body 13, sleeve 15 or any other tool utilized to operate the knotless anchor assembly 32. The compression member is designed to lock the tension member shown in FIG. 1B, tension member 18 and passing loop depicted in FIG. 5C or any other member used as a fixation member.

Additional instruments can be utilized in this method by attaching a sleeve 15 to the anchor body 13 and inserting a driver 16 through the sleeve 15 and into the anchor body recess 14, as shown in FIGS. 3A-3D. In this embodiment, the driver 16 and sleeve 15 assembly are used to introduce the anchor body 13 in the bone 30 or similar tissue that would act as a fixation point until the anchor body 13 is completely below the surface. The driver 16 is then removed while leaving the sleeve 15 attached to the anchor body 13. Next, the tension member 18 is inserted into the sleeve slot 29.

In an alternate embodiment, the anchor 10 may be introduced in the bone 30 or tissue with the driver 16 or sleeve 15 only.

In an alternate embodiment, the tension member 18, passing loop 20 or compression member 11 may be attached or connected to the anchor body 13 or knotless suture anchor assembly 32 at the time of anchor implantation. In this embodiment, the compression member 11 may or may not be connected to the introducing device.

The sleeve 15 may function as a driver 16 to insert an anchor 10 in the bone 30 or any other anatomy that requires a fixation device to perform a repair. The length of the sleeve 15 may vary depending upon the anatomical location, technique, tools used, type of surgery or other indications that may determine the length of the sleeve 15. The sleeve 15 may be manufactured using materials used to manufacture the knotless anchor assembly 32 that are defined herein but not limited to those materials and made by any manufacturing process used to manufacture anchor, tools or other typically used in the industry.

The amount of contact between the sleeve 15 and the anchor body 13 may vary depending on the amount of strength and contact area necessary for optimal insertion of the knotless anchor assembly 32. The sleeve 15 may be partially or completely cannulated or in instances may be solid with no cannulation. The size of sleeve recess 35 may vary depending on the fibers that may pass through the sleeve 15. The length of the sleeve recess 35 may vary and it may be partial or completely open on one or both sides or many surfaces. The inner surface 36 of the sleeve 15 may be partially or completely threaded or in the instances where the sleeve is solid with no cannulation the sleeve will not be threaded. In those instances, the sleeve 15 may also function as a driver to insert the anchor 10.

Similarly the anchor body recess 14 dimensions may vary depending on a variety of factors, including, but not limited to, the anatomy, location of repair its designed for, the number of fibers that may be needed to perform the repair, the surface area needed (e.g., the amount of surface area needed for sleeve contact), the strength of device depending on biomaterial or other anchor manufacturing material used, and the amount of contact if needed with the compression member 11. The anchor body recess 14 may assist with the passage of fixation members or tissue to complete the repair.

The lengths and dimensions of the driver 16 may vary depending on the anatomical locations, techniques, tools or other factors that may influence the size of the driver 16. The driver 16 may be solid with no cannulation or may be cannulated partially or completely or may have thread internally or externally. The external surface area may be modified depending on the size of the knotless anchor assembly 32 and the anatomical location its used in to improve the safety of the device and prevent failures while performing the repair.

As shown in FIGS. 4A-4C, a broach/pusher 19 broaches a passage into bone 30 while also urging the tension member 18 into the anchor body recess 14. The compression member 11 is inserted into the sleeve 15 and then threaded into the anchor body 13. Tightening the compression member 11 results in locking the tension member 18 motion inside the anchor body 13, while backing up the compression member 11 allows unlocking of the tension member 18 and adjusting its position (i.e. re-tensioning) before relocking it in place. The sleeve 15 is then removed. It is contemplated that the compression member 11 may be deployed or engaged with the tension member 18 with any secure mechanism other than threading.

In an alternate embodiment of the knotless anchor assembly 32, the compression member 11 may be connected to the anchor body 13 or may not need a secondary introduction process.

In yet another embodiment, the anchor body 13 or knotless anchor assembly 10 may be driven in the bone 30 or a surface needing fixation without an internal driver 16.

The broach/pusher 19 can be made out of the similar material used to manufacture the knotless anchor assembly 32 disclosed herein, but not limited to those materials, and may be made of other devices used in the industry.

The broach/pusher 19 is used to create channel in the soft tissue, bone, membrane, or graft. It is also used to transport the tension member 18 for further locking by the compression member 11. The broach/pusher 19 may also help with aligning of fibers or tension member 18 for optimal locking. The broach/pusher 19 may also be a part of the tool construct used to insert the anchor 10. The broach/pusher 19 may be used to create the channel or transport sutures or any other defined functions using different techniques which may vary from tapping, twisting but not limited to them. The broach/pusher 19 may be used independently of other tools e.g. absence of sleeve 15 to assist with the defined functions of the broach/pusher 19. The length, size, dimensions, design features may vary depending upon the anatomical location as long as the broach/pusher 19 is able to perform the defined functions. The broach/pusher 19 may be manufactured as one piece or two pieces or a multiple piece construct. The broach/pusher 19 may be partially or completely cannulated.

In an alternative method of urging the tension member 18 into the anchor body recess 14, the anchor 10 is assembled with the passing loop 20, as shown in FIGS. 5A-5D. The anchor 10 is driven into the bone 30 using the driver 16, and the tension member 18 is inserted into the passing loop 20, as shown in FIG. 5B. Next, the free ends 21 of the passing loop 20 are pulled to pull the tension member 18 into the anchor body recess 14, as shown in FIG. 5C. The compression member 11 is threaded into the anchor body 13 to lock the tension member 18 in place. The passing tension member 18 or passing loop 20 may be pulled out of the anchor 10 or left in place.

The compression member 11 may unlock the tension member 18 or fixation members by backing up or similar mechanism to disengage or loosen the tension in the fixation/tension members 18. The passing loop 20 may have a looped end and free ends 21 or may have loop on both ends or can be any mechanism of transporting the fixation or tension member or members 18 in the anchor body recess 14 or within the anchor body 13 for locking purposing by the compression member 11.

FIG. 5A depicts the passing loop 20, passing through the hole 33 on the pilot tip 12. In an alternate embodiment, the passing loop 20 or member designed for similar mechanism may be connected to the anchor body 13 or be with or in close proximity and enable passing of the tension members 18 for locking using the compression member 11. Again, backing up the compression member 11 allows unlocking of the tension member 18 and adjustment of its position (i.e. re-tensioning) before relocking it in place. The locking between the anchor body 13 and the compression member 11 may enable fixation of the tension members 18, fixation members, bone 30, graft, soft tissue, or gap fillers. The compression member 11 may interact with any of the aforementioned members to assist with fixation and repair/reconstruction for all embodiments taught herein.

It is not necessary for the tension members 18 or the passing loop 20 to pass through the hole 33 in the pilot tip 12 to perform its function which mainly is to position the tension members 18 in the recess to perform locking using the compression member 11.

The passing loop 20 may have single or multiple loops. The passing loop 20 may or may not have free ends. The passing loop 20 may be used to pass the tensioning member, graft, allografts, membrane, gap fillers. The passing loop 20 at times may be a part of the repair when locked with the compression members 11.

Figures 6A, 6B, 6C, 6D, 6E:
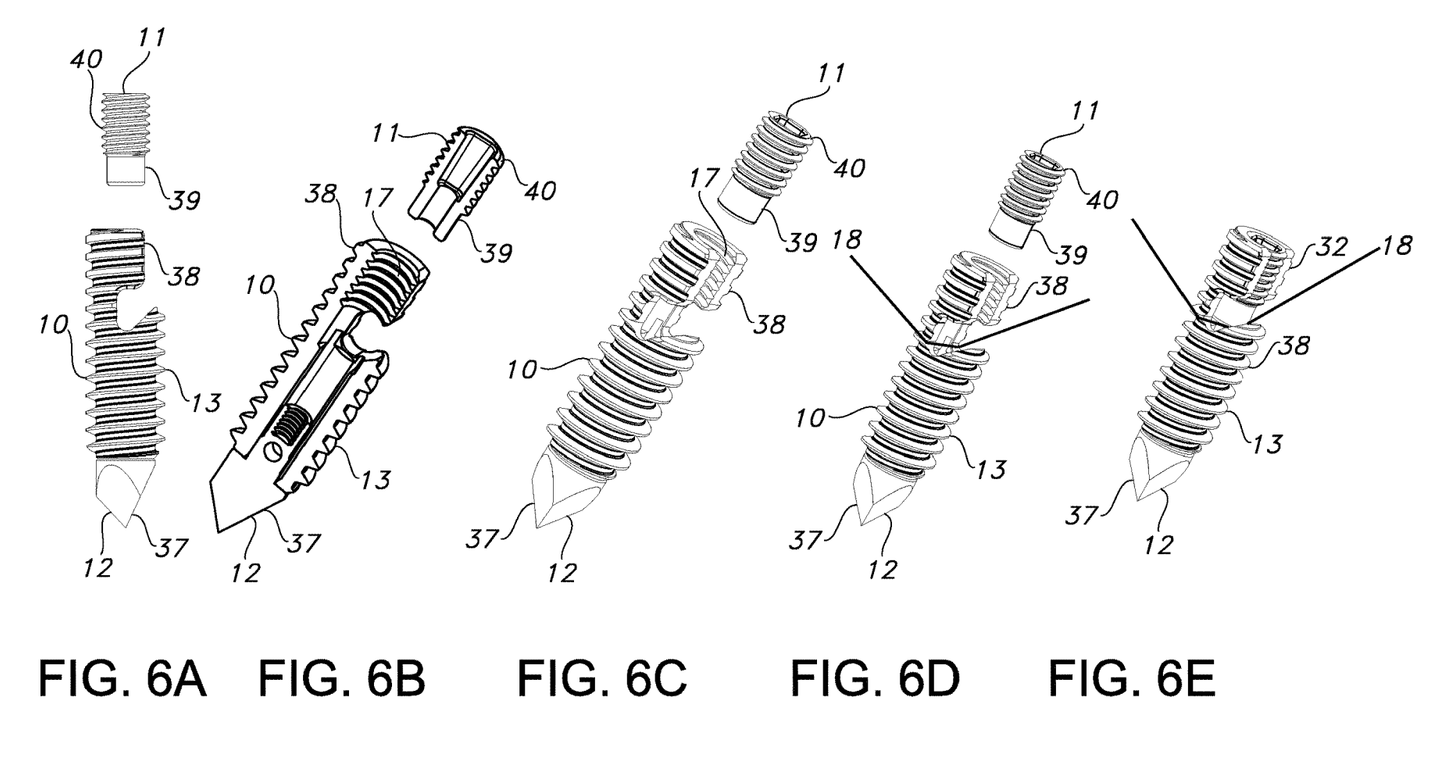
FIG. 6A depicts a perspective view of the second embodiment of the knotless anchor assembly.
FIG. 6B depicts a cross-sectional view of the second embodiment of the knotless anchor assembly.
FIG. 6C, depicts a perspective view of the second embodiment of the knotless anchor assembly.
FIG. 6D depicts a perspective view of the second embodiment of the knotless anchor assembly with passing loop.
FIG. 6E depicts a perspective view of the second embodiment of the knotless anchor assembly.

In a second embodiment of the knotless anchor assembly 32, the anchor body recess 13 is partially off center and has a generally J-shape, as shown in FIG. 6A-6D. The tension member 18 is passed through the anchor body recess 14, as shown in FIG. 6D.

Figure 7A:
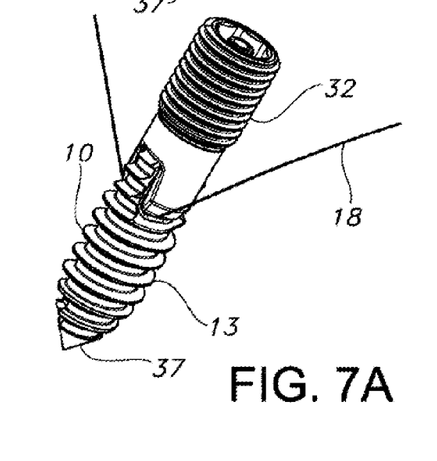
FIG. 7A depicts a perspective view of the third embodiment of the knotless anchor assembly.
Figure 7B:
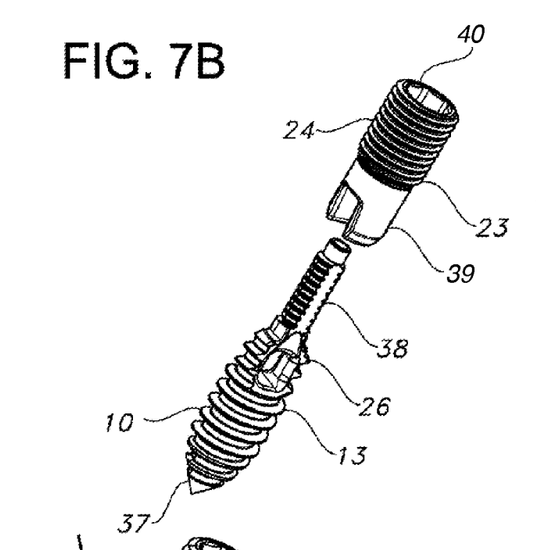
FIG. 7B depicts a perspective view of the third embodiment of the knotless anchor assembly.
Figure 7C:
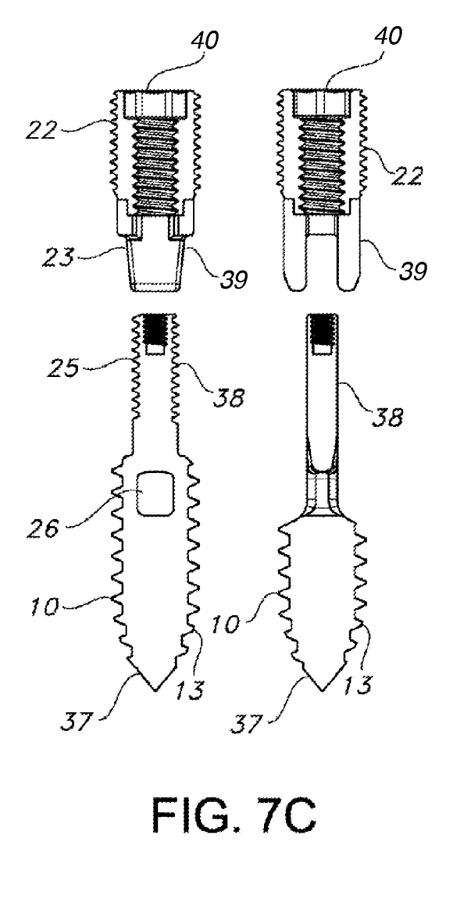
FIG. 7C. depicts a cross-sectional view of the third embodiment of the knotless anchor assembly.
Figure 7D:
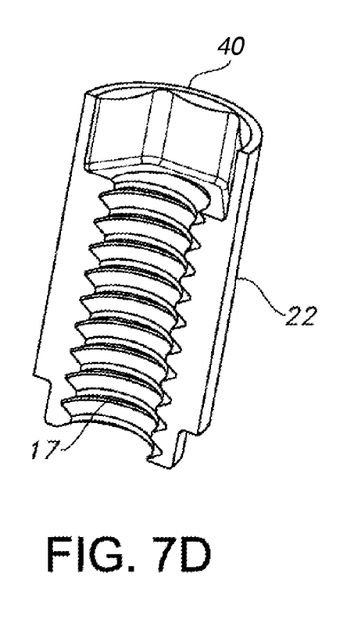
FIG. 7D depicts a perspective of the threaded portion of the third embodiment of the knotless anchor assembly with passing loop.
Figures 8A, 8B:
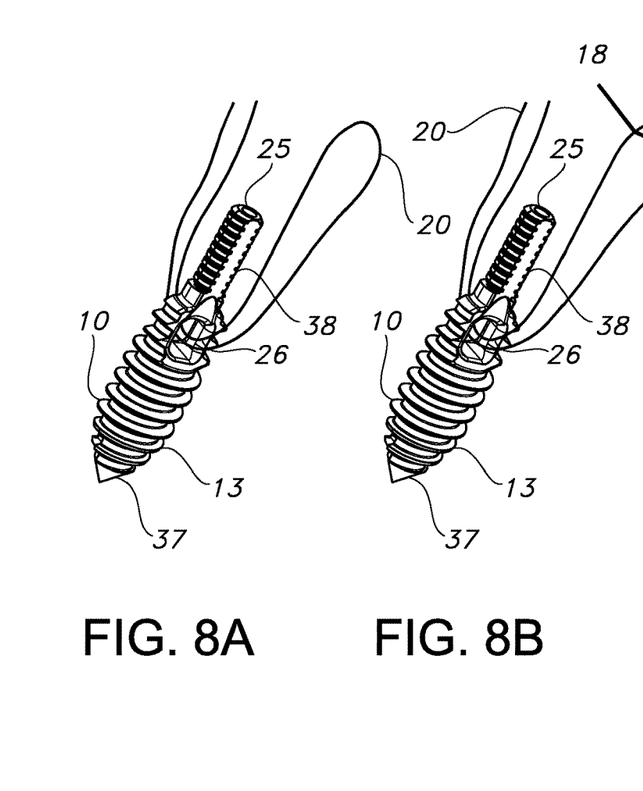
FIG. 8A depicts a perspective view of the third embodiment of the knotless anchor assembly.
FIG. 8B depicts a perspective view of the third embodiment of the knotless anchor assembly.
Figures 8C, 8D, 8E:
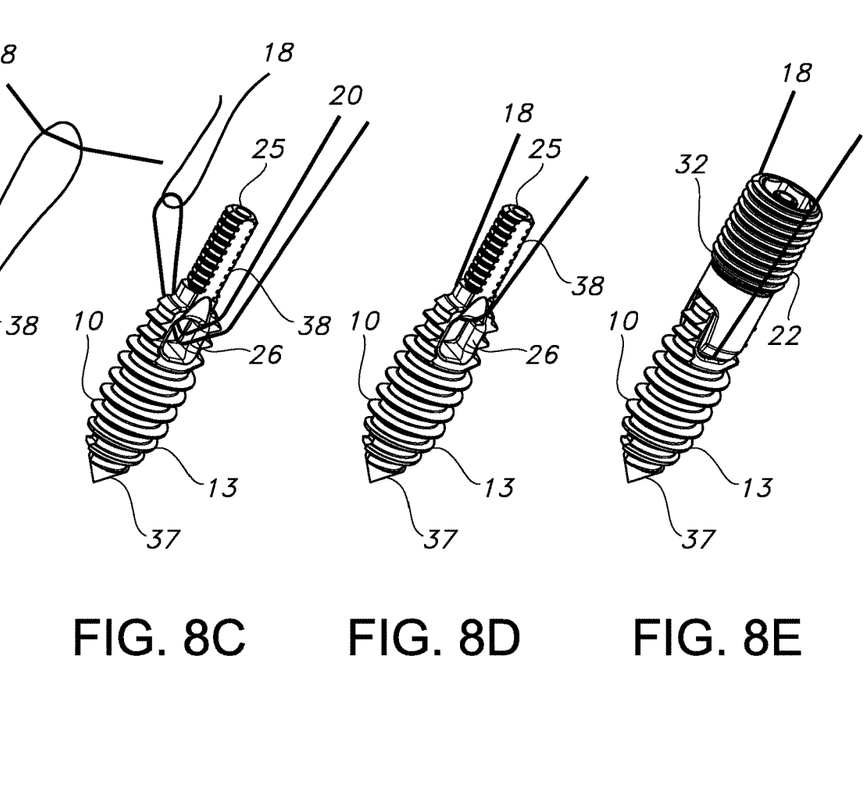
FIG. 8C. depicts a perspective view of the third embodiment of the knotless anchor assembly.
FIG. 8D depicts a perspective of the third embodiment of the knotless anchor assembly.
FIG. 8E depicts a perspective of the third embodiment of the knotless anchor assembly.
Figures 11A, 11B, 11C, 11D:
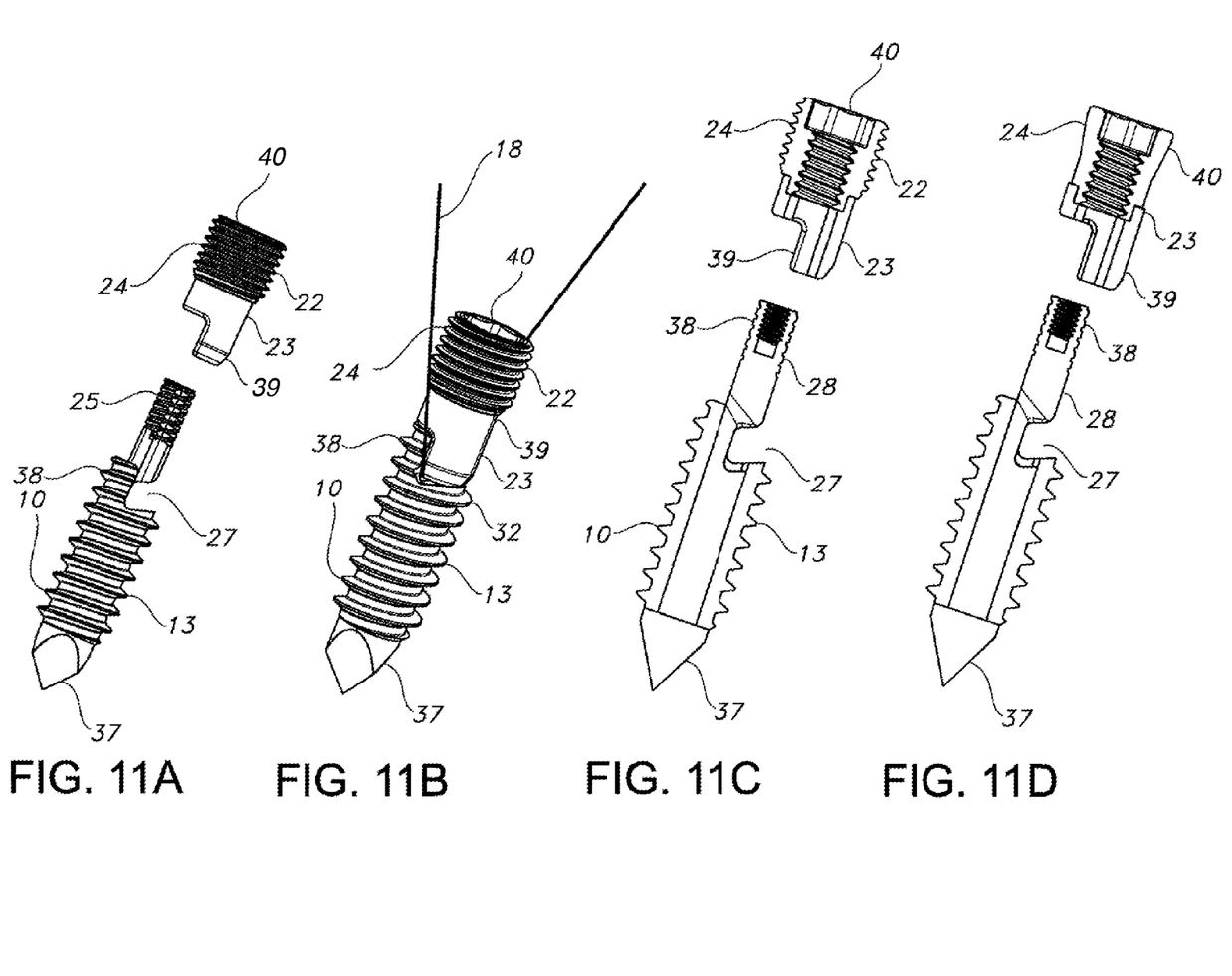
FIG. 11A depicts a perspective view of the sixth embodiment of the knotless anchor assembly.
FIG. 11B depicts a perspective view of the sixth embodiment of the knotless anchor assembly.
FIG. 11C depicts a cross-sectional view of the sixth embodiment of the knotless anchor assembly.
FIG. 11D depicts a cross-sectional of the sixth embodiment of the knotless anchor assembly.

In a third embodiment, the knotless anchor assembly further comprises a threaded portion 22 and a carriage 23, as shown in FIGS. 7A-7E. The carriage 23 can rotate relative to the threaded portion 22 but is prevented from rotating when engaged with the threaded stem 25 of the anchor body 13, as shown in FIGS. 7-8. When an alternate embodiment of the compression member 11, the locking assembly 24, is attached to the threaded stem 25 of the anchor body 13, the threaded portion 22 threads onto the threaded stem 25, while the carriage 23 translates on the stem 25 linearly without rotating, as shown in FIGS. 7A, 7D and 8E. It is contemplated that the outer part of the locking assembly 24 may be smooth as shown in FIG. 11D.

Figures 10A, 10B, 10C, 10D, 10E:
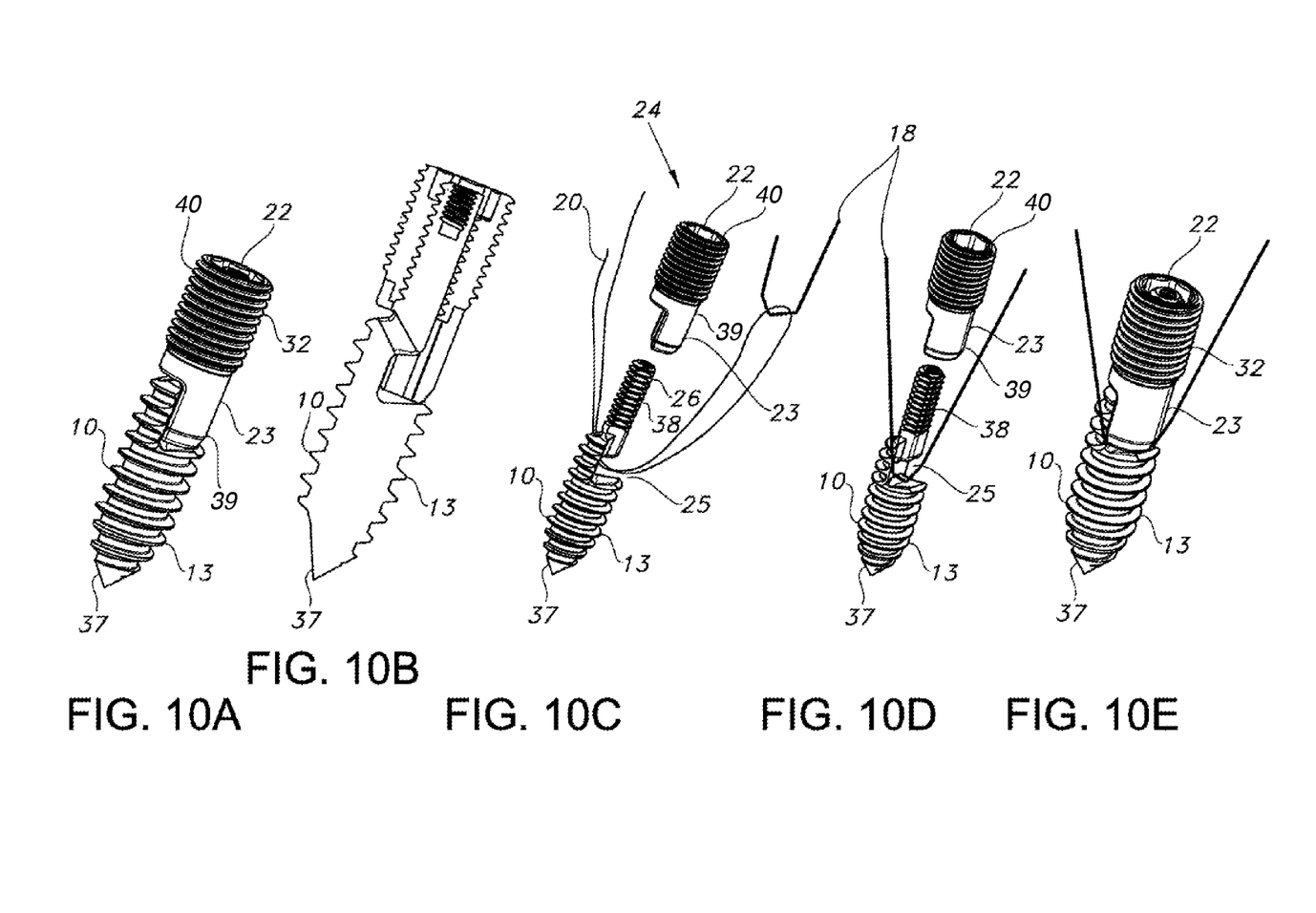
FIG. 10A depicts a perspective view of the fifth embodiment of the knotless anchor assembly.
FIG. 10B depicts a cross-sectional view of the fifth embodiment of the knotless anchor assembly.
FIG. 10C depicts a perspective view of the fifth embodiment of the knotless anchor assembly.
FIG. 10D depicts a perspective view of the fifth embodiment of the knotless anchor assembly.
FIG. 10E depicts a perspective of the fifth embodiment of the knotless anchor assembly.

The carriage 23 may be manufactured using any of the materials defined to manufacture the knotless anchor assembly 32, but not limited to the same. The carriage 23 may or may not have any threads. The carriage 23 may be partial or complete as shown in FIGS. 7 and 10. The lengths, dimensions may vary depending on the anatomical locations, techniques, tools or other factors that may influence the size of the carriage 23. The carriage 23 may or may not assist with locking the tension members 18. The carriage 23 may also create fixation points between itself and the anchor 10. The carriage 23 may be partial, as shown in FIGS. 10-11.

The threaded portion 22 may have internal and an external thread that preferably have equal pitches, so that the locking assembly 24 can thread into bone 30 as it is being threaded onto the threaded stem 25. Conversely, the locking assembly 24 only may only have internal thread or external thread with variable pitches, thread height, or other varying features. The smooth outside surface allows the tension member 18 to move more easily against it when re-tensioning or adjustments are needed.

Figures 9A, 9B, 9C, 9D, 9E:
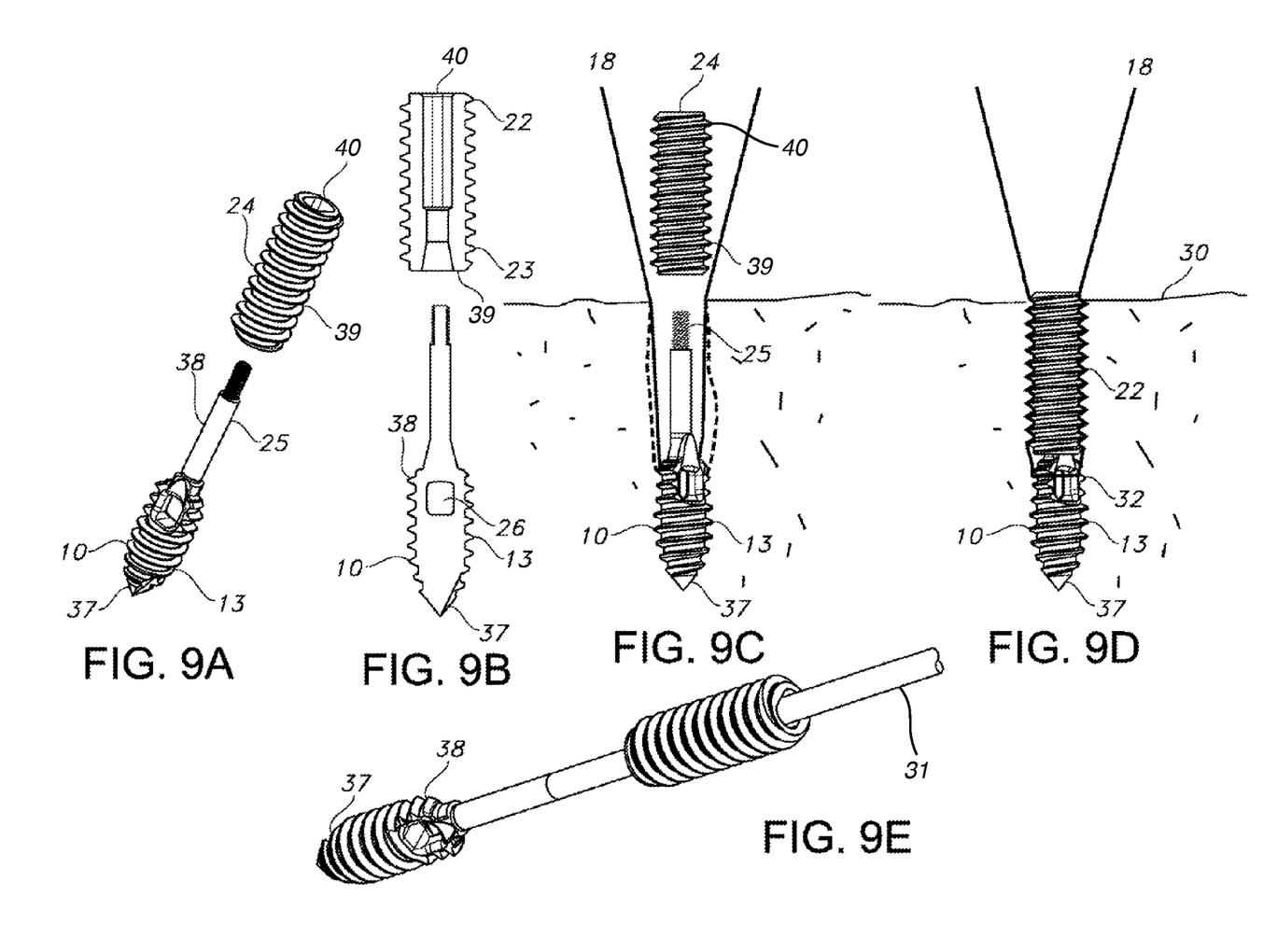
FIG. 9A depicts a perspective view of the fourth embodiment of the knotless anchor assembly.
FIG. 9B depicts a perspective view of the fourth embodiment of the knotless anchor assembly.
FIG. 9C. depicts a perspective view of the fourth embodiment of the knotless anchor assembly.
FIG. 9D depicts a perspective of the fourth embodiment of the knotless anchor assembly.
FIG. 9E depicts a perspective of the fourth embodiment of the knotless anchor assembly.

In this embodiment, the load passing loop 20 is inserted into the anchor body 13, and the anchor body 13 is driven into bone 30 until completely below the bone surface, as shown in FIGS. 8A-8E. The tension member 18 is inserted into the passing loop 20, which is pulled to pull the tension member 18 through the eyelet 26, as shown in FIGS. 9A-9C. Tension is applied to the tension member 18 as needed. To lock the tension member 18 in place, the locking assembly 24 is inserted and threated onto the threaded post 22, as shown in FIGS. 8D, 8E, 9C, 9D, both pinching it against the bone 30 and against the anchor body 13. Backing up the locking assembly 24 unlocks the tension member 18 and adjusts it (i.e. retention) before re-locking. When the alternate embodiment of the threaded portion is used, the tension member 18 may or may not only be locked/pinched between locking assembly 24 and anchor 10. In another embodiment of anchor 10 with carriage 23, the locking may happen between the carriage 23 and anchor body 13 only.

A fourth embodiment is contemplated similar to the third embodiment, but the locking member 24 is not threaded onto the anchor stem 25. Instead, the tension member 18 is locked by means of pinching it between the locking member 24 and bone 30 (the locking member 24 here acts as an interference screw), as shown in FIG. 9A-9E. The top of the anchor stem 24 may be threaded to facilitate attachment and use of the guide pin 31, as shown in FIG. 9E.

The lengths and dimensions of the guide pin 31 may vary depending on the anatomical locations, techniques, tools or other factors that may influence the size of the guide pin 31. The guide pin 31 may have partial or complete cannulation. The guide pin 31 may be solid and may have internal or external threads. The guide pin 31 may connect with the anchor body 10 or anchor stem 25 using the threads, as shown in FIG. 9E, press-fit or other mechanisms that are used in the industry to connect tools temporarily or permanently.

A fifth embodiment is also contemplated similar to the third embodiment, but instead of a closed eyelet 26, the anchor body 13 has a side-opening, as shown in FIG. 10A-10E.

A sixth embodiment is contemplated similar to the fifth embodiment wherein the anchor body 13 comprises two portions—an anchor body 13 and anchor inner core 28, as shown in FIG. 11A-11D. The anchor inner core 28 may be partial or complete.

Figure 12A:
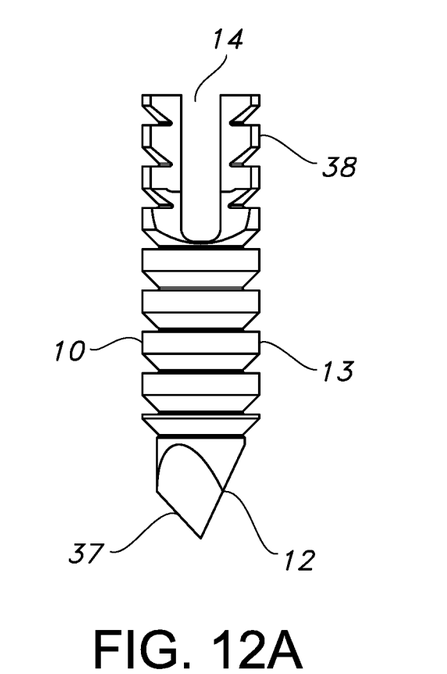
FIG. 12A depicts a perspective view of embodiment of an anchor with anchor body recess.
Figure 12B:
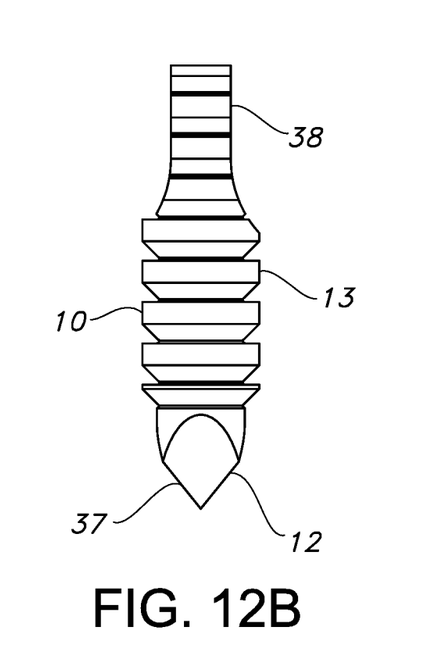

FIGS. 12A and 12B depict an embodiment of the knotless anchor assembly where the anchor body 10 is inserted by tapping the anchor 10 in the bone 30 or structure requiring the fixation point. The compression member 11, locking member 24, or knotless suture assembly 32 may follow the anchor body 13 to complete the locking.

FIGS. 12A and 12B represent embodiments of the anchor 10 where the tension member 18 can be tied around any part of the anchor 10, such as, an eyelet, hole, slot, cannulation, or recess, and driven on the bone 30 to complete the repair. The anchor 10 in this embodiment may contain an eyelet in the anchor body 13. If the tension member 18 is not tied it may be connected to the anchor body 11 using other techniques that may be utilized to complete the repair. The anchor 10 may also be inserting using techniques which may capture the tension member 11 outside the anchor body 10 and perform locking. A secondary fixation device may or may not be required to be passed to complete the repair.

The components described herein may be manufactured using standard procedures used in the industry, including, but not limited to, machining, molding, casting, 3D printing, etc.

Recess or eyelets or holes within the anchor 10, knotless anchor assembly 32, pilot tip 12 or any other member that completes the fixation may vary depending upon the anatomical location, number of fixation members required to perform the repair or if the fixation members also include grafts, membrane, gap fillers or other components that may have to be captured at the time of repair or if other devices are used in combination of this knotless anchor assembly 32 to complete the repair.

All embodiments disclosed herein allow repairs using knotless anchor assembly 32 performed in a knotless fashion. A surgeon or other user may tie knots with any or all of the embodiments or partial constructs taught herein.

It is contemplated herein for all embodiments of the knotless anchor assembly that any components may be manufactured out of polymers (including PEEK, PLA, PEKK, UHMWPE and others), metal or metal alloys (including Titanium, Cobalt, Molybdenum, Rhenium, Iron and their alloys), composites (including carbon fiber-, glass fiber-, any fiber-, barium sulfate- and metal-filled polymers), or ceramics (including oxide ceramics, nitride ceramics, diamond, bone, etc.). Tensioning member 18 is contemplated as being manufactured out of a variety of fibers or filaments including but not limited to polymer filaments (e.g. HMWPE, UHMWPE, PET, PTFE, PEEK, PEKK, PLA, PLLA, etc.), metallic filaments (e.g. Nitinol, Titanium, Titanium alloys, Tantalum, Stainless Steel, etc.) or organic filaments (e.g. Collagen, Silk, etc.) or other filaments such as carbon fiber or carbon nanotubes, etc. Tensioning member 18 is further contemplated to comprise, but not limited to, a coreless suture, a suture with a jacket and a central core, a tape or any other tension member available or contemplated. The length of the tensioning member 18 is contemplated as being between 150 mm and 1000 mm in length and more preferably between 300 mm and 1000 mm in length and most preferably between 250 mm and 750 mm in length but may chance depending on anatomical location, technique or instrumentation.

To prevent glove tears, surgeons can use hemostat forceps to roll the tensioning member 18 during a procedure utilizing the knotless anchor assembly 32.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all sub-ranges and individual values are intended to be encompassed. This invention is not to be limited by the embodiments disclosed, including any shown in the drawings or exemplified in the specification, which are given by way of example and not of limitation. Additionally, it should be understood that the various embodiments of the knotless anchor assembly described herein contain optional features that can be individually or together applied to any other embodiment shown or contemplated here to be mixed and matched with the features of that device.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A knotless anchor assembly comprising:
   an anchor defining a longitudinal axis and further comprising an anchor body having a distal end comprising a bone-engaging feature, a proximal end comprising an elongated post extending proximally along the longitudinal axis, and an anchor body recess traversing at least part of the anchor body between the distal end and the proximal end; and
   a compression member coupled with the elongated post, the compression member defining a longitudinal axis and further comprising a leading end portion rotatably coupled with a trailing end portion such that the leading end portion is configured to rotate relative to the trailing end portion, an external surface configured to interface with bone, and a central corridor extending through the leading end portion and trailing end portion through which the elongated post passes to couple the compression member with the anchor;
   wherein the compression member translates along the elongated post to secure a tension member associated with the anchor by pinching the tension member between the compression member and at least one of the anchor body and bone, such that the leading end portion advances along the elongated post linearly without rotating while the trailing end portion advances along the elongated post linearly with rotation.

2. The knotless anchor assembly of claim 1, wherein at least part of the compression member overlaps with the anchor body recess when the compression member is coupled with the anchor.

3. The knotless anchor assembly of claim 1, wherein the bone-engaging feature comprises external threads.

4. The knotless anchor assembly of claim 1, wherein the elongated post has external threads.

5. The knotless anchor assembly of claim 4, wherein the central corridor within the trailing end portion includes threads configured to mate with the external threads of the elongated post.

6. The knotless anchor assembly of claim 1, wherein the elongated post includes an external threaded portion and an external unthreaded portion.

7. The knotless anchor assembly of claim 6, wherein the external unthreaded portion extends longitudinally through the external threaded portion.

8. The knotless anchor assembly of claim 1, wherein the anchor body recess comprises an eyelet extending transversely through the anchor body.

9. The knotless anchor assembly of claim 1, wherein the anchor body recess comprises a side opening.

10. The knotless anchor assembly of claim 1, wherein the leading end portion has a smooth outer surface.

11. The knotless anchor assembly of claim 1, wherein the trailing end portion has a threaded outer surface.

12. A method of securing a member to bone in stabilization procedures, comprising:
    driving an anchor into bone such that the anchor is completely below the bone surface, the anchor defining a longitudinal axis and further comprising an anchor body having a first end comprising a bone-engaging feature, a second end comprising an elongated post configured to couple with a compression element, and an anchor body recess traversing at least part of the anchor body between the first end and the second end;
    inserting a tension element associated with the member into the anchor body recess;
    applying tension to the tension element;
    securing the tension element by advancing the compression element along the elongated post, the compression element defining a longitudinal axis and further comprising a leading end portion rotatably coupled with a trailing end portion such that the leading end portion is configured to rotate relative to the trailing end portion, an external surface configured to interface with bone, and a central corridor extending through the leading end portion and trailing end portion through which the elongated post passes to couple the compression member with the anchor;

wherein the compression member translates along the elongated post to secure the tension element by pinching the tension element between the compression element and at least one of the anchor body and bone, such that the leading end portion advances along the elongated post linearly without rotating while the trailing end portion advances along the elongated post linearly with rotation.

13. The method of claim 12, wherein the step of inserting the tension element into the anchor body recess includes the sub-steps of:

inserting a passing loop through the anchor body recess;
associating the tension element with the passing loop; and
pulling the passing loop through the anchor body recess such that the tension element is pulled through the anchor body recess.

14. The method of claim 12, further comprising the step of adjusting the tension element after performing the step of securing the tension element, the step of adjusting the tension element comprising the sub-steps of:

releasing the tension element by translating the compression element along the elongated post in a direction of the trailing end;
adjusting the tension applied to the tension element; and
re-securing the tension element by advancing the compression element along the elongated post such that the tension element is secured by pinching the tension element between the compression element and at least one of the anchor body and bone.

15. The method of claim 12, wherein the leading portion has a smooth outer surface.

16. The method of claim 12, wherein the secured member is at least one of tissue, ligaments, sutures, grafts, allografts, membrane, gap fillers, tension members, and bone.

* * * * *